US00PP13174P2

(12) United States Plant Patent
Hitzigrath

(10) Patent No.: US PP13,174 P2
(45) Date of Patent: Nov. 5, 2002

(54) POINSETTIA PLANT NAMED 'FISMARBLE SILVER'

(75) Inventor: Joachim Hitzigrath, Cuernavaca (MX)

(73) Assignee: Florfis AG, Binningen (CH)

( * ) Notice: Subject to any disclaimer, the term of this patent is extended or adjusted under 35 U.S.C. 154(b) by 12 days.

(21) Appl. No.: 09/753,628

(22) Filed: Jan. 4, 2001

(65) Prior Publication Data

US 2001/0011384 P1 Aug. 2, 2001

(51) Int. Cl.[7] ..... A01H 5/00

(52) U.S. Cl. ..... Plt./303

(58) Field of Search ..... Plt./303

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of Poinsettia plant named 'Fismarble Silver' characterized by having intense salmon-pink bract color with a narrow white margin; tight, relatively large inflorescence with slightly upward directed bracts; light greyish-green, white margined foliage; relatively compact and well-branched plant habit; medium (mid season) flowering response; and good after-sale keeping quality of the bracts and the cyathia.

1 Drawing Sheet

BACKGROUND OF THE INVENTION

The present invention relates to a new and distinct cultivar of Poinsettia plant known by the cultivar name 'Fismarble Silver', and botanically known as *Euphorbia pulcherrima*. 'Fismarble Silver' was derived from a naturally occurring mutation in the variety 'Marblestar' (U.S. Plant Pat. No. 9,685). 'Marblestar' is characterized by salmon-pink, white margined bracts, intense green foliage, and medium tall, round plant habit.

The mutation was discovered by the inventor, Mr. Joachim Hitzigrath, in a greenhouse in Cuernavaca, Mexico, among a group of stock plants in the spring of 1999. One plant had developed a mutated branch with variegated foliage. Several cuttings were taken from the branch by the inventor, and sent to Hillscheid, Germany, where they were rooted and grown out. The resulting plants were examined in the autumn of 1999 and proved to be absolutely uniform. This was confirmed in the horticultural trial cultivation conducted on a larger scale from August to December 2000.

BRIEF DESCRIPTION OF THE INVENTION

The following traits have been repeatedly observed and are determined to be basic characteristics of 'Fismarble Silver' which in combination distinguish this Poinsettia as a new and distinct cultivar:

1. Intense salmon-pink bract color with narrow white margin;
2. Tight, relatively large inflorescence with slightly upward directed bracts;
3. Light greyish green, white margined foliage;
4. Rlatively compact and well-branched plant habit;
5. Medium (mid season) flowering response; and
6. Good after-sale keeping quality of the bracts and the cyathia.

'Fismarble Silver' has not been observed under all possible environmental conditions. The phenotype may vary significantly with variations in environment such as temperature, light intensity, and day length. The following observations, measurements and comparisons describe plants grown in Hillscheid, Germany, under greenhouse conditions which approximate those generally used in commercial practice.

Of the may commercial cultivars known to the inventor, the most similar in comparison to 'Fismarble Silver' is the parent cultivar 'Marblestar' and the cultivar 'Fisflirt Silver' (U.S. Plant Pat. No. 11,585). In contrast to 'Marblestar', 'Fismarble Silver' has variegated foliage that is lighter and more greyish-green in color. 'Fismarble Silver' produces foliage with narrow, irregular, white margins. Furthermore, 'Fismarble Silver' grows somewhat more slowly than 'Marblestar' and the 'Fismarble Silver' plant habit is more compact and lower by about 30% when grown under the same cultivation scheme as 'Marblestar'. The flowering response time of 'Fismarble Silver' is similar to that of 'Marbelstar'. The 'Fismarble Silver' inflorescence is only slightly smaller than 'Marblestar'. 'Fismarble Silver' has slightly more intense bract color than 'Marblestar'. The 'Fismarble Silver' bracts have whitish margins with a very slight pink hue while those of 'Marblestar' are cream-colored with a very slight brownish hue.

In comparison to 'Fisflirt Silver', 'Fismarble Silver' has a more intense bract color and differently shaped bracts. While bracts of 'Fisflirt Silver' are flat and borne horizontally, those of 'Fismarble Silver' are folded and somewhat upward directed. Furthermore, plants of 'Fismarble Silver' are marketable about 8 days earlier than 'Fisflirt Silver'.

BRIEF DESCRIPTION OF THE DRAWING

The accompanying color photographic drawing shows typical inflorescence and foliage of 'Fismarble Silver', with colors being as true as possible with illustrations of this type. The photograph shows a mature potted plant and a flowering, branched plant.

DETAILED BOTANICAL DESCRIPTION

The plants described herein were grown in a greenhouse in Hillscheid, Germany, in the fall of 1999. Rooted cuttings were planted into 14 cm pots on Jul. 23, 1999 and were pinched after two weeks, leaving 8 nodes. The minimum temperature was 21° C. until September 22, and 18.5° C. to December. Shading was not applied, the flowers were developed under natural day-light conditions.

Observations and measurements were mainly taken in early December 2000, at the beginning of full flowering. In the following description color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'FISMARBLE SILVER'.

Parentage: Naturally occurring mutation of 'Marblestar'.

Plant:

*Form.*—Shrub, self-branching.

*Growth habit.*—Compact, pinched plants are bushy, wide and round, and relatively low. Height (without pot): 26.5 cm. Width: 44 cm. Average number of branches: 8–9. Average number of inflorescence: 8.

*Stem color.*—(Light) green, RHS 143 A.

*Rooting.*—About 20 days

*Blooming habit.*—Begin under natural short day conditions in fall: Botanically (cyathia open): around December 1. Commercially (bracts colored, saleable): around December 1.

*Flowering response time.*—About 9.5 weeks.

*Flowering season.*—Up to 5 weeks.

Foliage:

*Shape.*—Ovate to elliptical, with obtuse to rounded base, acuminated tip, and with very weak lobes.

*Margin.*—Mainly entire, irregular crenation may occur in places.

*Texture.*—Upper surface: Smooth or slightly wrinkled (rugose), only weakly veined. The vein color is light green, about RHS 138 C. Lower surface: Smooth, except for the slightly protruding midrib and finer side veins, which are arranged in a pinnate pattern, the color of the veins is very light green, RHS 145 C.

*Size.*—Leaf blade: 12 cm long, 7.5 cm wide on average. Petiole: 5.5–6.5 cm long.

*Leaf color.*—Generally a light, slightly greyish, and near the margins slightly marbled green, and with narrow, irregular, white margins. Upper surface: main color, RHS 138 A, small, lighter spots, RHS 148 D margin, white, RHS 155 D. Lower surface: main color, RHS 137 C–D. margin: RHS 150 D.

*Petiole.*—Color: Upper side: whitish to very light brown, near RHS 159 A. Lower side: light green, RHS 144 C, a slight infusion of anthocyanin may occur.

*Aspect of leaves.*—Horizontally or slightly upward directed.

*Disease resistance.*—Typical, no special observations made.

Flowering description:

*Whole inflorescence.*—Tight arrangement of medium sized bracts, which are slightly upward directed.

*Keeping quality.*—Relatively good, no tendency to drooping of the bracts, no fading of the bract color.

*Diameter.*—23 cm on average.

*Number of bracts per infl.*—10–11.

*Bracts.*—Shape: ovate to elliptical, with rounded base, almost no lobes, and with acuminated tip. Size: 9.5 to 10.5 cm long, 5.8–6.0 cm wide.

*Texture.*—Surface: Somewhiat wrinkled, rugose. The veins are hardly visible at the upper surface, while they slightly protrude at the lower surface. The vein color corresponds closely to the bract color on the upper surface, while it is lighter on the lower surface: very light pink, RHS 36 C–D.

*Color.*—Generally intense salmon-pink, slightly marbled, and with narrow, irregular, white margin. Upper surface, main color: Between RHS 43 C and RHS 43 D. Margin: RHS 36 D or lighter. Lower surface, main color: Salmon-pink, RHS 43 C.

*Petiole.*—10–15 mm long, pink colored, about RHS 48 B.

*Cyme.*—About 25 mm wide, 10–12 or, under favorable conditions, even more cyathia in a tight cluster.

*Diameter of the single cyathium.*—5–6 mm.

*Color of the cyathium.*—Light green, RHS 142 A top salmon-pink, RHS 43 C.

*Nectar cups.*—1–2 honey cups per cyathium, 5–6 mm wide, yellow to light orange colored.

Reproductive organs:

*Stamens.*—Few, light red, turning brown, abortive, usually no pollen.

*Pistils.*—Whitish style, and pink, 6-lobed stigma.

*Ovaries.*—Typical shape, triangular, 3 ovules.

*Fertility.*—Seed set was not observed, but the typically developed pistils indicate, that the plant might be used as a seed parent, while it is sterile as a pollen parent.

I claim:

1. A new and distinct Poinsettia plant named 'Fismarble Silver', substantially as illustrated and described.

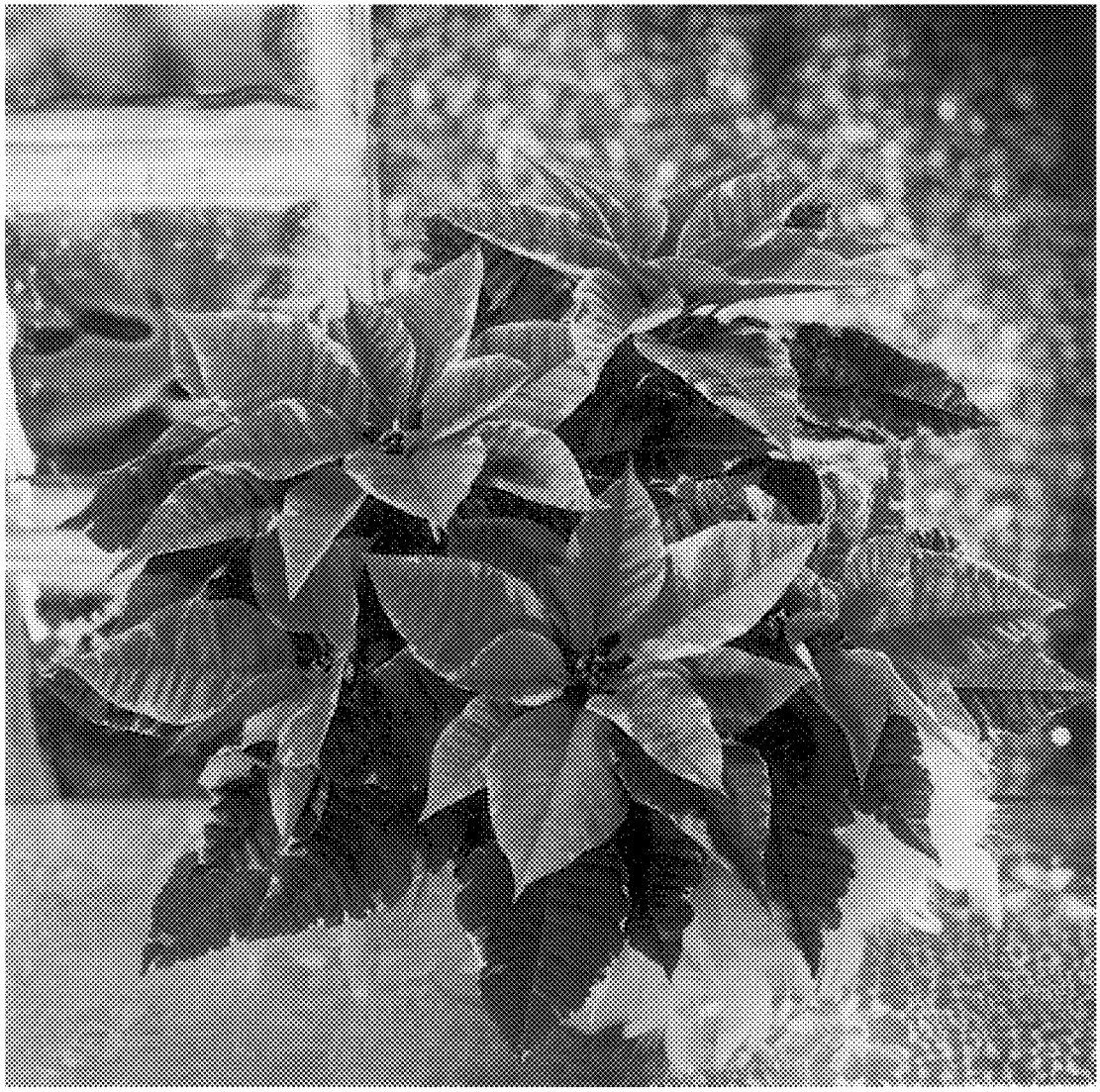

* * * * *